United States Patent [19]
Kallick

[11] Patent Number: 5,795,563
[45] Date of Patent: Aug. 18, 1998

[54] IDENTIFICATION OF AN EXOGENOUS INTRA-ERYTHROCYTIC BACTERIUM IN PATIENTS HAVING SYSTEMIC LUPUS ERYTHEMATOSUS, AND TREATMENT

[75] Inventor: Charles A. Kallick, Lemont, Ill.

[73] Assignee: Sphingomonas Research Partners, L.P., Lemont, Ill.

[21] Appl. No.: 763,709

[22] Filed: Dec. 13, 1996

Related U.S. Application Data

[63] Continuation-in-part of Ser. No. 707,472, Sep. 4, 1996, abandoned.

[51] Int. Cl.$^6$ .......................... A61K 49/00; A61K 31/43
[52] U.S. Cl. ...................... 424/9.361; 424/9.362; 424/9.363; 514/192; 514/199; 514/200
[58] Field of Search .................. 424/2, 3, 9.361, 424/9.362, 9.363; 514/192, 199, 200

[56] References Cited

U.S. PATENT DOCUMENTS

| | | | |
|---|---|---|---|
| 4,329,331 | 5/1982 | Kallick | 424/8 |
| 5,585,243 | 12/1996 | Aster et al. | 435/7.21 |

OTHER PUBLICATIONS

Lahita, R.G., *Systemic Lupus Erythematosus*, Churchill, Livingston, New York, p. XXIX (1987).
Taurog, et al., *Intern. J. Derm.*, 20:149–158 (1981).
Crow, et al., "Etiologic Hypothesis for Systemic Lupus Erythematosus", Lahita, *Systemic Lupus Erythematosus*, Churchill, Livingston, New York, p. 54 (1987).
Pincus, *Arthr & Rheum*, 20:149–158 (1982).
Kallick, et al., *Nature New Biology*, 236:145–146 (1972).
Kallick, et al., *Arthr & Rheum*, 23:197–205 (1980).
Miller, et al., eds., *Immunity to Blood Parasites in Animals and Man*, Plenum Press, New York, pp. 155–188 (1977).
Franklin, et al., *Southwestern Vet.*, 15:131–139 (1962).
Brown, et al., *J. Lab. Clin. Med.*, 34:1404–1410 (1949).
Scheff, et al., *Infec. Dis.*, 98:113 (1956).
Ristic, et al., *J. Vet. Res.*, 19:37 (1958).
Dubois, *Lupus Erythematosus*, 2d ed., U.S. California Press, Los Angeles (1974).
Krier, *Ann. Rev. Microbiol.*, 325–338 (1981).
Coon, *so. Amer. J. Surgery*, 155:391 (1988).
*Goodman and Gilman's The Pharmaceutical Basis of Therapeutics*, 8th ed., McGraw–Hill, Inc., New York, pp. 1085–1892 (1993).
Genarro, et al., eds., *Remington's Pharmaceutical Sciences*, 18th ed., Mack Publishing Co., Easton, PA, pp. 1193–1200 (1990).
*Physician's Desk Reference*, PDR®, 48th ed., Medical Economics Data Production Co., Montavale, NJ, Product Category Index, pp. 203–204, and individual listings (1994).
*The Merck Index*, 11th ed., Merck & Co., Rahway, NJ, (1989) individual listings.
Morrison, et al., *J. Clin. Microbiol.*, 24(5):835–855 (1986).

*Primary Examiner*—Kevin E. Weddington
*Attorney, Agent, or Firm*—Welsh & Katz, Ltd.

[57] ABSTRACT

Intra-erythrocytic exogenous bacterial structures or parasites seen by giemsa and phase contrast microscopy in several patients with systemic lupus erythematosus (SLE) and not in controls were identified as bacteria. Treatment of an SLE patient is contemplated with an antibacterial amount of a rifamycin in conjunction with an antibacterial amount of either a macrolide such as clarithromycin or a third generation cephalosporin such as cefpodoxime that is itself more preferably used in conjunction with an adjuvant amount of probenecid.

5 Claims, 3 Drawing Sheets

IDENTIFICATION OF AN EXOGENOUS INTRA-ERYTHROCYTIC BACTERIUM IN PATIENTS HAVING SYSTEMIC LUPUS ERYTHEMATOSUS, AND TREATMENT

This is a continuation-in-part of application Ser. No. 08/707,472, filed Sep. 4, 1996, now abandoned, whose disclosures are incorporated by reference.

TECHNICAL FIELD

The present invention relates to identification of the presence of an exogenous structure within human erythrocytes or bone marrow cells and treatment thereof, and more particularly to an assay for the presence of an exogenous bacterial structure or parasite within the erythrocytes of patients having systemic lupus erythematosus (SLE) and treatment of such patients to lessen or eliminate the erythrocytic or bone marrow load of those bacterial structures.

BACKGROUND OF THE INVENTION

Systemic lupus erythematosus (SLE) is a protean disease of unknown etiology which affects multiple organs. Lahita, R. G. *Systemic Lupus Erythematosus*, Churchill, Livingston, N.Y. (1987) page XXIX. Although there is a marked similarity to an infectious entity, an exhaustive search for an etiologic agent has not yielded any proven candidates that fulfill the criteria for causation of this disease. Crow et al., "Etiologic Hypothesis for Systemic Lupus Erythematosus," in Lahita *Systemic Lupus Erythematosus*, Churchill, Livingston, N.Y. (1987) page 51 ff. There is general agreement that tissue and organ injury in SLE is mediated by immune phenomena. Unexplained at this time is the predilection of SLE for females. Taurog et al., *Intern. J. Derm.*, 20:149–158 (1981).

Early descriptions of SLE before the advent of suppressive therapy suggested sepsis, and included fever, striking constitutional symptoms and high mortality. Crow et al., "Etiologic Hypothesis for Systemic Lupus Erythematosus," in Lahita *Systemic Lupus Erythematosus*, Churchill, Livingston, N.Y. (1987) page 54. Recently, many viral etiologic agents have been sought; none have been convincingly demonstrated. Pincus, *Arthr & Rheum*, 20:149–158 (1982). More recently the characterization of soluble products of bacteria and mycoplasmas with unique capacities to perturb immune systems have led to new considerations in regard to the infectious trigger of SLE.

Intra-erythrocyte organisms with characteristics like the Anaplasmataceae that were thought to be Haemobartonella-like were first suggested as exciting exogenous agents in SLE by Kallick et al., *Nature New Biology*, 236:145–146 (1972). The Anaplasmataceae family of bacteria are Proteobacteria of the order Rickettsiales. That report was further developed by a later report of antigenic similarities between SLE or lupus nephritis and diseases caused by *Anaplasma marginale*, an intra-erythrocytic parasite of cattle, and a member of the family Anaplasmataceae. Kallick et al., *Arthr. Rheum.*, 23:197–205 (1980).

Exogenous intra-erythrocytic structures seen in the same erythrocyte by giemsa staining and phase contrast microscopy, which were identical or very similar in appearance to *Anaplasma marginate*, have been observed in most patients with SLE. However, because the number of such structures seen in erythrocytes of SLE patients is very small, their presence has been unconfirmed by electron microscopy, until the present study. For example, the number of infected erythrocytes is usually less than 0.1 percent of observed erythrocytes in fixed thin blood films.

Based upon available data, which describe the pathology of SLE as tissue destruction associated with antibody formation and the development of antibodies against many body tissues as well as pathogens such as Epstein-Barr virus, and assuming that Anaplasmataceae or similar intra-erythrocytic pathogens are present in an uncontrolled parasitemia in SLE, a pathological mechanism can be deduced that contains, at least in part, a continued antigenic stimulation of the B-cell immune mechanism. The Anaplasmataceae were thought to offer an ideal putative model of infection, in that, based on studies by the inventor, above, they present an approximately 1 percent parasitemia or less level in systemic lupus erythematosus patients.

The Anaplasmataceae have been extensively studied in animals, and although they affect erythrocytes as a primary organ, their pathogenic potential appears to be primarily or exclusively mediated by immune mechanisms primarily identified as humoral. *Immunity to Blood parasites in Animals and Man*, Miller et al. eds., Plenum Press, New York (1977) pages 155–188. In animal disease, antibiotics control the primary pathologic event, hemolytic anemia, only if given early in the course of the illness. Late in the course of animal illness the hemolytic anemia is mediated by antibody formation and antibiotics do not appear to affect the course of the usually studied hemolytic anemia.

In animals, arthritis and long-term effects of illness after infection have not been studied or reported. However, in some animals that suffer hemolytic anemia such as adult bulls, chronic arthritis and anemia have been reported. In the veterinary literature, an antibiotic that appears to suppress some of the clinical manifestations of these organisms is tetracycline or one of its analogues. Franklin et al., *Southwestern Vet.*, 15:131–139 (1962).

Several humans with SLE or connective tissue disease have been treated with tetracycline (doxycycline) in preliminary work of the inventor based on the presumption of Anaplasmataceae parasitemia. Three patients are exemplary.

The first was a 17 year old female with severe SLE and nephritis who experienced a lysis of fever within a week of therapy with disappearance of Haemobartonella-like agents from the circulating erythrocytes as observed by acridine orange and fluorescent antibody determination. This patient was not subsequently followed.

The second patient is a male with SLE who has been taking tetracycline for his lupus for 10 years. He stated that his fever, joint pains, and other symptoms disappeared while he was taking tetracycline. He had first been given the antibiotic for treatment of another infection and noted it caused amelioration of his SLE.

The third is a patient who has mixed connective tissue disorder resembling SLE but with a negative ANA titer. This patient went into remission of her symptomatology after 3 weeks of therapy with tetracycline and has remained in clinical remission for the subsequent 3 months. It is of interest that in addition to marked subjective improvement of this last patient, C-reactive protein became negative after tetracycline therapy was begun.

Subsequent to these studied patients, a large number of other patients with SLE have received chronic therapy with tetracycline or its derivatives. These treatments have been on a compassionate basis by the patients' own physicians, or as part of a study approved by an institutional review board, but not completed. Most of such treatments have resulted in amelioration of the disease state, with complete remission, or a trend in such amelioration. That study, done at Cook County Hospital, Chicago, Ill., was terminated before the results, as analyzed, were shown to be statistically significant. The results appeared to be based on the small numbers analyzed.

A current patient studied is a splenectomized female with SLE who had a large number of parasitized erythrocytes beginning with about 16 percent. She has been on doxycycline with informed consent for 16 months with initial and continued improvement. Because she has enough intra-erythrocytic parasites to be counted, her course of treatment has been followed and electron microscopy was carried out. When examined in December 1995, she still had about 1.1 percent parasitized erythrocytes seen by giemsa staining and phase contrast microscopy.

Aureomycin, a tetracycline-like drug, has been proposed as a treatment for rheumatoid diseases in the past by T. Brown and co-workers and others, who treated a variety of patients with arthritis and lupus with claims of some degree of success in the 1940's. [Brown et al., *J. Lab. Clin. Med.*, 34:1404–1410 (1949); Scheff et al., *Infec. Dis.*, 98:113 (1956)] Those studies were not controlled, and have not been repeated. These theoretical and observed phenomena suggest that tetracycline may be of benefit in the syndrome of SLE.

Present therapy of SLE is based upon heavy steroid use with immunosuppressives and/or plasmapheresis. It is of interest that Anaplasmataceae infections in animals are, almost uniquely among infectious diseases, ameliorated by steroids. [Scheff et al., *Infec. Dis.*, 98:113 (1956); Ristic et al., *J. Vet. Res.*, 19:37 (1958)]

No presently used therapy is completely satisfactory, and, although the life expectancy of lupus patients has been considerably increased by present therapy, the ravages of therapeutic side effects and the constant fatigue takes a severe toll in well being, general health, and increased morbidity and mortality of the estimated 500,000 Americans with this disease. Dubois, *Lupus Erythematosus*, 2d ed., U.S. California Press, Los Angeles (1974).

Figure 1:
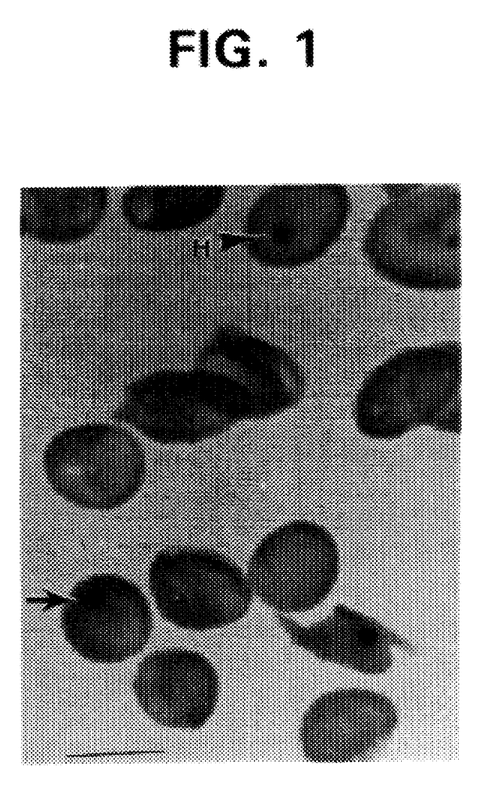
FIG. 1 is a thin blood film from the patient of the Example stained for one hour with filtered giemsa stain. This patient was splenectomized and had systemic lupus erythematosus. Several individual erythrocytes are visualized. The stained structure within the erythrocyte indicated by the arrow is the unidentified infectious bacterium. The structure in another erythrocyte designated "H" is a Howell-Jolly body often seen in splenectomized patients. A Howell-Jolly body can be differentiated from the bacterium by size and phase refraction but not by staining characteristics. Original magnification ×630.
Figure 2:
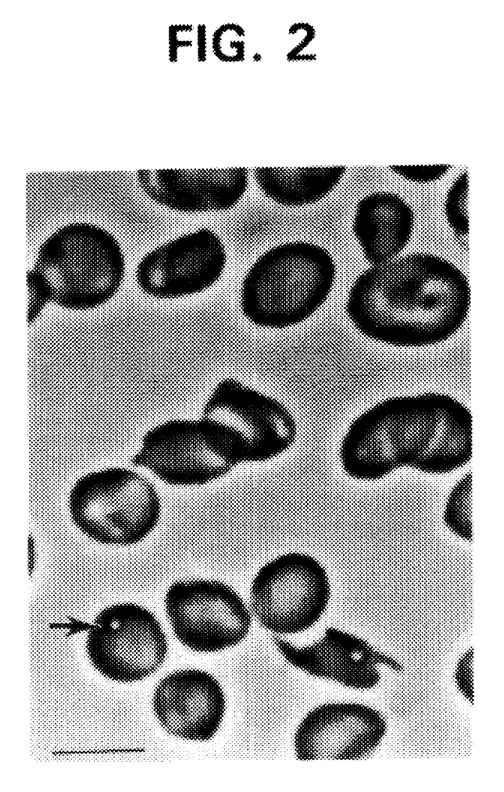
FIG. 2 is the same field of erythrocytes of the patient as seen in FIG. 1. The same erythrocytes are visualized, but the optical view is by phase contrast. In this mode, the giemsa-stained bodies are poorly visualized. Doubly refractile structures occupy the same positions and locations within the erythrocytes of those structures designated as the unidentified infectious bacteria, as seen with phase contrast optics. The structure of FIG. 1 designated "H" is absent in the phase contrast view as the Howell-Jolly structure does not contain a retractile body. Original magnification is ×630.
Figure 3:
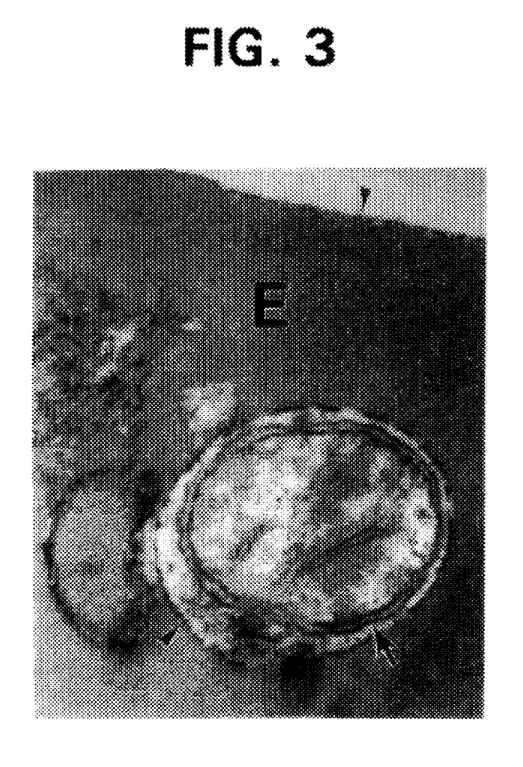
FIG. 3 is an electron micrograph showing a small portion of an erythrocyte from the same patient as in FIGS. 1 and 2. The area designated "E" is the matrix of the erythrocyte. The small arrow above and to the right of the "E" designates the erythrocyte membrane. The large arrow designates the double membrane enclosing the exogenous, infectious bacterium, and appears to have some of the characteristics of a gram-negative bacterial membrane. The limiting membrane of the vacuole layer surrounding the bacterium is designated by the unmarked wedge near the left-hand side of the micrograph, and morphologically resembles erythrocyte membrane. The original magnification ×65,000.

The spleen is regulatory in removing nuclear remnants and other intra-erythrocytic particles from erythrocytes, and in Anaplasmosis as well as malaria, splenectomy causes a recrudescence of clinical disease and parasitemia. Kreier, *Ann. Rev. Microbiol.*, 325–38 (1981). Splenectomy is an infrequently used treatment for the thrombocytopenia seen in some patients with SLE. Coon, *So. Amer. J. Surgery*, 155:391 (1988). However, the one splenectomy patient noted before was found to have parasitemias of erythrocytes with intra-erythrocytic phase contrast-visible retractile bodies in up to about 16 percent of her studied erythrocytes (FIGS. 1 and 2). These intra-erythrocytic bodies were very similar or identical to those seen in bovine *A. marginale* infection.

It would therefore be beneficial if the stainable exogenous structures found in the erythrocytes of SLE patients could be accurately identified, readily assayed for and eliminated from a patient's blood in that it is believed that those exogenous structures are the active, causative agent for SLE. The description that follows describes a treatment regimen that eliminates those exogenous bacterial structures from an SLE patient's blood.

In 1891 Howell described intra-erythrocytic bodies that occurred in splenectomized patients and animals. The appearance of these bodies that now bear the name Howell-Jolly bodies followed within a few hours or days of splenectomy. The elegant drawings of Dr. Howell, whose findings have been subsequently confirmed by others with modern methods including electron microscopy, have amptly demonstrated this phenomenon. The spleen in the normal patient removes the few nuclear remnants that are not absorbed or extruded in the bone marrow.

Howell-Jolly bodies are described as about 1 μ in diameter in an eccentric position in the erythrocyte. The bodies seen in anaplasmosis and in the patients with SLE are approximately 0.5 μ and have phase refractile characteristics that are not described in Howell-Jolly bodies. It is believed that the site of generation of the agents seen in SLE patients' erythrocytes is in the normoblasts or other cells of the bone marrow. These agents are normally removed by the spleen, but in the splenectomized patient are constantly circulating until the erythrocyte is senescent and destroyed in the reticulo-endothelial system. These particles in the normoblasts appear to have heretofore escaped detection because they morphologically resemble the normal metamorphosis of the normoblast, but are smaller.

BRIEF SUMMARY OF THE INVENTION

It has now been found that the giemsa- and acridine orange-stainable and phase contrast microscopy visible exogenous structures or parasites found in the erythrocytes of SLE patients are neither Rickettsiae nor Anaplasmatacea, but may be a presently unidentified member of the α-purple bacteria or another previously unclassified agent. In accordance with that finding, a process for treating SLE patients to remove the erythrocyte-parasitizing exogenous bacterial structures has been found.

Thus, this invention contemplates a process for treating a patient whose erythrocytes contain exogenous structures stainable with acridine orange or giemsa and are visible in phase contrast microscopy, such as a patient having systemic lupus erythematosus. That process comprises administering to the patient an antibacterial amount of a third generation cephalosporin or a macrolide in connection with an antibacterial amount of a rifamycin. In preferred practice, an adjuvant amount of probenecid is administered in conjunction with the administration of the third generation cephalosporin.

Most preferably, all three medicaments are administered in conjunction with each other when the cephalosporin is used. The administration of the macrolide or third generation cephalosporin plus a rifamycin is preferably repeated periodically. Clarithromycin is a particularly preferred macrolide, whereas cefpodoxime proxetil, a prodrug form of cefpodoxime, is a particularly preferred third generation cephalosporin, and rifampin or rifabutin is the preferred rifamycin.

BRIEF DESCRIPTION OF THE DRAWINGS

In the drawings forming a part of this invention.

The present invention has several benefits and advantages.

One benefit of the present invention is that it provides a process for treating a patient with SLE to lessen or remove the etiological bacteria from the erythrocytes of an SLE patient.

An advantage of the invention is that its process of treatment can be carried out with an antibacterial agent whose safety in humans has already been demonstrated.

Still further benefits and advantages of the present invention will be apparent to a skilled worker from the description that follows.

DETAILED DESCRIPTION OF THE INVENTION

A 30 year old African American female patient who had been splenectomized presented with the symptoms of systemic lupus erythematosus (SLE) in 1993. Examination of her blood indicated that about 16 percent of her erythrocytes contained exogenous bacterial structures or parasites that were stainable with giemsa and acridine orange and were refractile in phase contrast microscopy. Similar exogenous bacterial structures or parasites have also been found in the erythrocytes of other SLE patients, albeit at a lower level of infection involving about 0.1 percent of the erythrocytes. A blood sample received from another splenectomized patient from Norway evidenced parasitization of about 0.6 percent of the erythrocytes.

Inasmuch as the erythrocytes of the SLE patients examined have been found to contain these giemsa- and acridine orange-stainable exogenous bacterial structures or parasites, and such exogenous bacterial structures are not present in the erythrocytes of healthy patients or persons suffering from other diseases so far examined, it is believed that those parasites are the infective agent that causes SLE.

In accordance with recognized methods of determining the presence of an infectious agent in human specimens, a study was devised to assay whether the same organism was identifiable in other patients with SLE and not in controls. Thus, blood was collected from patients with SLE and matched controls, and mixed with a small quantity of EDTA that had been filtered through a 0.2 micron filter. Of the SLE patients studied, almost all exhibited the paratization.

SLE affects every organ system and this is consistent with an intra-erythrocytic organism carried in a small number of erythrocytes that may be capable of infecting cells other than erythrocytes. After processing in the reticulo-endothelial system of a patient with SLE, products from the breakdown of constantly circulating bacteria are capable of inducing B cell stimulation, which can account for the high levels of antibodies seen in SLE.

These organisms have now been found in the majority of patients with SLE, but have escaped detection and culturing by investigators over the years. In almost all SLE patients examined, this new organism parasitizes less than one percent of erythrocytes, and the methodology of examining human blood films is crude unless very careful technique is used. Both giemsa and Wright's stains must be filtered at each staining or the precipitate can be confused with intra-erythrocytic bodies.

For example, stock giemsa stain was mixed with supplied buffer at a ratio of 2 ml to 50 ml buffer. The stain was filtered onto the previously fixed thin blood film through a 0.2 micron filter. The stain must not be allowed to stand for more than the time needed for staining. The slide was immersed in the diluted stain for one hour, after which it was washed in de-ionized water and air dried.

The blood was examined on a Zeiss microscope through an objective with phase contrast optics. Each identified particle was viewed through a high power light field under oil immersion.

The exogenous intracellular structures of the unknown bacteria are observed as blue gray bodies usually in the marginal position and are about 0.4 to about 0.5 micron in longest dimension, whereas Howell-Jolly bodies are larger and are not phase contrast refractile. (FIG. 1). Verification that the exogenous bacterial structures are not artifacts is made by switching to phase contrast microscopy without moving the stage. The blue grey structure under phase contrast appears as a doubly refractile structure in the same erythrocyte in the same location (FIG. 2). These intra-erythrocyte structures can be also be confused with Heinz bodies, Howell-Jolly bodies (that are not refractile as is seen in FIG. 2), nuclear remnants, or simply be overlooked if not carefully sought.

Acridine orange can also be used as a stain for the exogenous bacterial structures. In that case, the blood film is fixed with saline to which 10 volume percent formalin has been added. After complete fixation for 24 hours, the film is examined under indirect fluorescent microscopy. Intraerythrocytic structures containing RNA fluoresce bright orange and are usually present in the marginal position within an erythrocyte.

The quantification of percentage of erythrocytes parasitized was made by counting ten fields within a square defined by an optically projected prism, determining the number of parasitized erythrocytes within the ten fields, and dividing the total number of parasitized erythrocytes by the total number ×100. This product was identified as the percentage of parasitized erythrocytes.

The standard method for staining of *Anaplasma marginale* using giemsa stain was used here. One could not be sure of seeing an artifact unless phase contrast microscopy was used to confirm each individual structure identified. Only after dual viewing, was the observed blue grey body accepted as a structure within the erythrocyte stroma.

Experimental infection of animals with Anaplasma is used for study of that entity, and veterinary hematologists have not relied on phase microscopy, because they see parasitemias of 50 to 80 percent. Some investigators in this field were unaware that the organisms could be seen more easily by phase contrast microscopy.

The presumed flooding of the reticuloendothelial system by the degenerative products of the unidentified bacteria affords a ready explanation for the spectrum of autoantibodies that characterize the extensively studied spectrum of B and T cell activation in SLE.

Treatment Process

The present invention contemplates treatment of a patient whose erythrocytes contain exogenous bacterial structures that are stainable with acridine orange and with giemsa, and are also visible with phase contrast microscopy, such as a patient suffering from systemic lupus erythematosus (SLE). That treatment comprises administering to that patient an antibacterial amount of a rifamycin along with an antibacterial amount of a macrolide or a third generation cephalosporin. In more preferred practice, an adjuvant amount of probenecid is administered in conjunction with the administration of the third generation cephalosporin.

SLE patients are often treated with a steroid compound such as prednisone as a palliative. That treatment is maintained during the antibacterial treatment and as long as is required.

Macrolides are hydroxylated macrocyclic lactones having 12 to 20 atoms in the primary ring. Although more than thirty macrolides are known, only erythromycin, its analogues and derivatives are clinically important, and the word macrolide is used herein to mean such compounds. A macrolide can be administered orally or parenterally, and again oral administration is preferred.

As used herein, a derivative of erythromycin has a biological activity similar to that of erythromycin itself, and a macrocyclic ring structure and pendant saccharide moieties that are the same as erythromycin, but additionally has one or more erythromycin substituent groups reacted with another moiety to form a functional group different from that present at the same position in erythromycin, such as one or more erythromycin hydroxyls being etherified with a methyl group or esterified with an acetyl or propionyl group in the derivative. Exemplary erythromycin derivatives include clarithromycin (methyl ether), erythromycin 2'-acetate octadecanoate (2'-acetate, stearate salt), erythromycin estolate (2'-propanoate dodecylsulfate salt) and the like. Clarithromycin is particularly preferred.

An erythromycin analogue is a compound that has a biological activity similar to that of erythromycin itself, a macrocyclic ring structure that is different from erythromycin and contains two atoms more or less in the macrocyclic ring than does erythromycin, while having similar ring substituents to erythromycin or an erythromycin derivative. An exemplary erythromycin analogue is azithromycin.

Clarithromycin is available as BIAXIN™ FILMTAB® tablets from Abbott Laboratories. These commercial tablets each contain 250 mg or 500 mg of clarithromycin. Usual dosages are 250 to about 4000 mg per day in one to four about evenly spaced oral administrations. A daily administration of a total of about 500 to 1000 mg in two to four administrations is preferred with rifampin for synergetic activity.

Clarithromycin can be administered without regard to a patient's stomach contents; i.e., given on a full or empty stomach. On the other hand, the bioavailability of erythromycin is lessened when that drug is administered to a patient who had recently eaten.

Cephalosporin compounds are grouped in the art by so-called generations that are classed by activity rather than structure. Exemplary first, second and third generation classifications are found in *Goodman and Gilman's The Pharmaceutical Basis of Therapeutics*, 8th ed., McGraw-Hill, Inc., New York (1993) pages 1085–1092; *Remington's Pharmaceutical Sciences*, 18th ed., Gennaro et al. eds., Mack Publishing Co., Easton, Pa. (1990) pages 1193–1200; *Physician's Desk Reference*, PDR®, 48th ed., Medical Economics Data Production Co., Montvale, N.J., Product Category Index, (1994) pages 203–204, and individual listings; and *The Merck Index*, 11th ed., Merck & Co., Rahway, N.J. (1989), individual listings.

Third generation cephalosporins are noted to be generally less active against gram-positive organisms than are first generation cephalosporins, but are much more active against gram-negative organisms, particularly against Enterobacteriaceae.

One structural feature shared by many third generation cephalosporins is a second ring joined to the beta-lactam-sulfur-containing 4,6-fused ring that usually characterizes cephalosporins, with that second ring being linked to the first ring by an alkoxyiminoacetyl amino group in which the alkoxy group is methyoxy or an $-O-C_1-C_4-$ alkylenecarboxyl group such as a $-CH_2CO_2H$ or $-C(CH_3)_2CO_2H$ group. It is noted, however, that cefuroxime, a second generation cephalosporin, also contains that structure, and that some third generation cephalosporins such as cefoperazone, cefpimizole and cefsulodin do not contain an alkoxyiminoacetyl group. In addition, moxalactam, another third generation cephalosporin, has an oxygen rather than a sulfur atom in the 4,6-fused ring. Thus, again, a third generation cephalosporin compound useful herein is functionally defined as such in the art.

Exemplary third generation cephalosporin compounds useful in this aspect of the invention include cefoperazone, cefmenoxime, ceteferam, cefpimizole, cefodizime, cefixime, cefotaxime, cefsulodin, ceftazidime, ceftizoxime, ceftibuten, cefxiofur, ceftriaxone, cefuzonam, moxalactam and cefpodoxime. Most of the third generation cephalosporins are administered by injection. However, oral administration is preferred. Orally active and administrable third generation cephalosporins include cefixime, cefteram, ceftibuten and cefpodoxime. Use of cefpodoxime is particularly preferred, and that third generation cephalosporin is usually administered as an ester prodrug called cefpodoxime proxetil. This compound is available from The Upjohn Company as tablets or as an oral suspension under the name VANTIN™.

The third generation cephalosporin, however administered, is administered in an usual antibacterial amount. That amount differs with each drug, with the usual antibacterial amounts being available in the PDR®. For the particular preferred cefpodoxime proxetil, that amount is about 200 to about 800 milligrams (mg) and more preferably about 400 to about 800 mg per day for adults. A usual duration of administration for this third generation cephalosporin is 14 days, although that time may be lengthened.

In preferred practice, the third generation cephalosporin is administered in conjunction with the administration of an adjuvant amount of probenecid. Probenecid is available from Merck & Co. under the name BENEMID®, and is a well-known adjuvant for beta-lactam antibiotics such as penicillins and cephalosporins, and acts to raise the blood level of the beta-lactam by inhibiting excretion in urine.

Typical oral adult administrations are about 500 mg to about 2 grams (g) daily, more preferably about 250 to about 1000 mg daily, with a usual dose being 250 mg twice a day for one week, and then 500 mg twice a day thereafter.

Probenecid and the third generation cephalosporin are usually administered at the same time. However, simultaneous administration is not necessary so long as plasma levels of about 30 to about 200 micrograms per milliliter (µg/mL) of probenecid in plasma are achieved when the third generation cephalosporin is in the bloodstream. Simultaneous oral administration is preferred.

It is necessary to co-administer a rifamycin with the other two medicaments. The phrase "a rifamycin" is meant to include rifamycin itself as well as rifamycin derivatives as are discussed below. Rifamycin is a broad-spectrum antibiotic produced by *Streptomyces mediterranei* that is active against most gram-positive organisms and has variable activity against gram-negative organisms such as *Escherichia coli* and Pseudomonas. Rifamycin and its derivatives also have intracellular bactericidal activity.

Rifampin is a particularly preferred rifamycin derivative that is available from Marien Merrell Dow as RIFADIN®, and can administered perorally or by injection in an antibacterial amount. Capsules for oral administration are available that contain 150 or 300 mg of rifampin per capsule. Usual adult oral administrations are 600 mg once per day, usually with water about one hour before a meal, with dosages of about 450 to about 900 mg per day being contemplated.

Rifabutin, available under the trademark MYCOBUTIN® from Pharmacia-Upjohn, is also a preferred rifamycin derivative. Rifaentine, available from Marion Merrell Dow under the trademark RIFATER®, and rifamide, also available from Marion Merrell Dow, are other rifamycin derivatives that can also be used.

One way to assess how long to continue administration of the macrolide or third generation cephalosporin in conjunction (along) with one or both of the above drugs is to continue administration of the drugs until the stainable, phase contrast microscopically visible, exogenous bacterial structures seen in SLE patient's erythrocytes prior to treatment are absent from the erythrocytes. This duration of administration may take as long as about 120 days, the average lifetime of an erythrocyte. Periodically repeated administrations of two or three drugs that encompass the average lifetime of an erythrocyte are thus contemplated and are preferred.

It is to be understood that the macrolide or third generation cephalosporin, probenecid and rifampin need not be administered via the above-noted commercially available forms. Rather, those drugs can be compounded into a composition for administration to a SLE patient using well-known pharmaceutical techniques.

A contemplated composition can be a solid or a liquid. The active ingredients can also be individually admixed as a suspension of solids in a solid or liquid physiologically tolerable carrier, or dissolved as a solute or suspended in the carrier, or a combination thereof.

Physiologically tolerable carriers are well-known in the art. Exemplary of liquid carriers are sterile aqueous solutions that can contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes. These latter carriers are exemplified by Ringer's Injection, Dextrose Injection, Dextrose and sodium chloride Injection and Lactated Ringer's Injection.

Liquid compositions can also contain liquid phases in addition to and to the exclusion of water. Exemplary of such additional liquid phases are glycerin, vegetable oils such as sesame oil or cottonseed oil, and water-oil emulsions.

Exemplary solid carriers include those materials usually used in the manufacture of pills or tablets, and include corn starch, lactose, dicalcium phosphate, thickeners such as tragacanth and methylcellulose U.S.P., finely divided SiO₂, polyvinylpyrrolidone, magnesium stearate and the like. Additionally, the solid carrier can include biodegradable and nonbiodegradable polymers, polypeptide carriers, affinity carriers such as AFFI-GEL® 601 (phenyl boronate resin available from Bio-Rad Laboratories, Richmond, Calif.), liposomes and synthetic polymers, as are known in the art. Antioxidants such as methylparaben and propylparaben can be present in both solid and liquid compositions, as can sweeteners such as cane or beet sugar, sodium saccharin, sodium cyclamate and the dipeptide methyl ester sweetener sold under the trademark NUTRASWEET® (aspartame) by G. D. Searle Co.

It is particularly preferred, however, to utilize the orally administratable tablet and capsule forms of a macrolide such as clarithromycin as are available from the before-named manufacturers with rifampin or third generation cephalosporin, such as cefpodoxime proxetil, probenecid and rifampin.

EXAMPLE

The following example is presented to illustrate certain aspects of the invention and is not intended to limit the scope of the invention.

SLE Patient Treatment

Patient History

Patient RJ is a 30 year old African-American female who became ill with easy bruising, fatigability and what was found to be thrombocytopenia. Upon failure of conventional therapy, she was splenectomized with improvement of her thrombocytopenia.

The patient developed the symptomatology of SLE in 1993, and was found to have thrombocytopenia, leukopenia, hypocomplementemia, elevated anti-nuclear antibodies (ANA), and antibodies to double-stranded DNA (anti-dsDNA) above 1000. She developed severe vasculitis that was only minimally controlled with high doses of prednisone, azathioprine (IMURAN®) and various other immunoregulatory agents. In 1994, her blood was examined for evidence of what was thought to be Anaplasmataceae, and found to have exogenous intra-erythrocytic bacterial structures that were morphologically indistinguishable from *Anaplasma marginale*.

Because of the severe disease of the patient, a trial of doxycycline was begun with express written consent of the institutional review board (IRB) and the patients's informed consent. The patient was begun on doxycycline at a dose of 100 mg twice daily. She was instructed to refrain from meals containing calcium, magnesium or milk products while on the medication, and was cautioned about the effects of sunlight on patients with this antibiotic.

Doxycycline

The patient began subjective improvement within three weeks of therapy, and this continued until the doxycycline was discontinued after 15 months. During this time she was able to increase her physical activity to walks of 3 to 5 blocks in the city. She noticed marked subjective improvement but this still required her treatment with azathioprine, and prednisone in doses ranging from 20 to 60 mg daily. Severe oral exfoliative lesions appeared from time to time that were not related to Herpes or Candida infection as established by negative cultural and other diagnostic methods.

During this time, sequential examination of her blood showed a rapid drop of parasitized erythrocytes, counted on the same microscope by a combination of phase contrast and careful giemsa staining. The drop in parasitized erythrocytes proceeded from more than 15 percent to less than 1 percent (about 0.7 percent) over one year, but plateaued at one year at approximately one percent. When the number of parasites began a slow rise to 1.1 percent in spite of continued therapy, concern began for the presence of developing resistance to the antibiotic.

Selection of Antibiotics

Because of the previously noted published activity of the third generation cephalosporins against intra-erythrocytic pathogens, the intra-erythrocytic location of the presumed pathogen, the likely slow metabolic rate of cell division (deduced from the slow fall of parasites under doxycycline), and the protected intra-erythrocytic environment on the organism, the following antibiotic combination was decided upon:

1. Cefpodoxime 400 mg twice daily with meals. Cefpodoxime is an orally active cephalosporin that has third generation activity. Cefpodoxime is only 15 to 40 percent protein bound, and has activity against *E. Coli* and Klebsiella at 1 µg. In addition, its serum activity after a 400 mg dose was 4 to 6 µg, and this could be doubled with concomitant probenecid.

2. Probenecid at 500 mg twice daily. This was used to increase the blood levels to approximately twice their expected values.

3. Rifampin 300 mg twice daily. Rifampin was chosen because of its ability to penetrate cell walls, its oral dosage facility, and its known synergy with most antibiotics acting on cell walls.

The unidentified organism was presumed to have a peptidoglycan cell wall and likely susceptibility to a third generation cephalosporin, as noted by Morrison et al., *J. Clin. Microbiol.*, 24(5):853–855 (1986). Intravenous therapy with any of the third generation cephalosporins for 4 months would have the same effect, but because of that impracticality, the orally available cefpodoxime was chosen. Cefixime has similar characteristics and activities among the oral third generation cephalosporins, but is 90 percent protein bound, would presumably have problems traversing the erythrocyte membrane, and is less preferred.

Another consideration was the total number of organisms in this patient's blood. At the time of initiation of therapy, 1.1 percent of her erythrocytes had a parasite. The mode of activity of doxycycline is bacteriostatic, which presumes that one would wait for erythrocyte senescence and destruction for its elimination. Cephalosporins with or without rifampin are bacteriocidal, and there was concern that with the intracellular death of so many parasites, they would be expelled from the erythrocyte, (or the erythrocyte would degenerate), and the reticuloendothelial system would be instantly flooded with bacterial bodies, no longer shielded by erythrocyte membrane. The lesson of the Jarisch-Herxheimer reaction in Syphilis appeared to have similarities.

Results of Therapy With Antibiotic Combination of Cefpodoxime and Rifampin With Probenecid The doxycycline was stopped on December 23, 1995, and the above combination therapy was begun on the next day. On the eighth day of treatment, the patient experienced chills, fever to 104° F., vomiting and diarrhea with dehydration that required her hospitalization. Her face suddenly became flushed with a markedly lupus-like rash. Her stool was negative for *C. difficile* toxin, and she responded to intravenous therapy with fluids. Examination of her blood showed that the parasites had dropped to about 0.7 percent from the previous about 1.1 percent. The antibiotic treatment was stopped on Dec. 31, 1995.

The patient thus experienced a reaction quite consistent with the Jarisch-Herxheimer response or an allergic reaction to the cephalosporin. The latter allergic reaction was confirmed after a restart of the above three-drug antibiotic treatment caused an accelerated reaction on Jan. 10, 1996. At that time about 1.4 percent of the patient's erythrocytes were parasitized. A Jarisch-Herxheimer reaction to the sudden release of bacterial parasites cannot be completely ruled out.

The patient experienced a reaction quite consistent with an allergic delayed hypersensitivity reaction, and on re-challenge appeared to have an accelerated reaction with continuous severe cutaneous burning. It is also possible that she experienced a Jarisch-Herxheimer reaction, although this is considerably less likely. This change in parasitemia indicated that approximately 40 percent of the intracellular parasites had been released or destroyed after 4–5 days of therapy with cefpodoxime and rifampin with probenecid.

The above 3-drug therapy was ceased and the patient was again treated with doxycycline on Jan. 12, 1996, after the level of exogenous bacterial structures (parasites) in her erythrocytes again climbed to about 1.8 percent. After about one week on doxycycline, the percentage of parasitized erythrocytes declined to about 1.6 percent.

On Jan. 20, 1996, doxycycline treatment was stopped and the patient began treatment with clarithromycin at a daily dose of 1000 mg, with equal doses taken two times each day. Her erythrocytes were examined microscopically as in FIGS. 1 and 2, and the percentage of parasitized erythrocytes was noted to decrease from about 1.6 to about 1.1 percent by Jan. 24, 1996, with some bacterial cell margins being indistinct at that time. The presence of indistinct bacterial cell margins often indicates bacterial damage. No adverse reaction to the clarithromycin was noted, and that treatment was continued with the percentage of parasitized erythrocytes dropping to about 0.7 percent by Jan. 31, 1996.

The patient discontinued all antibiotic therapy in May of 1996. When examined after two months, manifestations of Systemic Lupus Erythematosus had markedly increased after a previously prolonged period of remission. The patient was very ill when examined in July of 1996, with constitutional symptoms of her disease, possibly exacerbated by an allergic reaction to the medications empirically administered for what was interpreted as cutaneous vasculitis. Her parasitemia had increased to 1.3 percent from a previously recorded 0.6 percent and intra-erythrocytic parasites were readily visible by giemsa staining and phase contrast microscopy.

Clarithromycin was begun at a dose of 500 mg. twice daily, in July and after one month of treatment, clinical remission of symptoms was almost complete. The level of parasitemia had dropped to 0.2 percent. This level was rechecked for accuracy after two days and was verified as correct, and represented the lowest level of parasitemia ever observed in this patient.

In September 1996, rifampin at a dose of 300 mg twice daily was administered with the clarithromycin. Within three weeks, significant and marked changes had occurred in the visualized parasites with blood of the patient as follows. Clinical improvement of the patient was parallel to these changes 1) the numbers of previously visualized parasites had fallen to 10 percent of their previous number, 2) approximately 70 percent of the parasites had changed when viewed microscopically: (a) some were fragmented, (b) some had changed their optical characteristics so that they were refractile under bright field microscopy, a characteristic which had never before been observed, and (c) under phase contrast optics, they changed to a larger retractile intra-erythrocytic structure unlike any had heretofore been observed.

All the changes seen strongly suggested bacterial dissolution and death.

Because a structure was still maintained within the erythrocyte, it was protected from the reticuloendothelial cells and was not absorbed as would happen normally to an extra-cellular bacterial structure.

This patient had been continually treated palliatively with prednisone throughout her illness. That prednisone dosage has been 20 mg per day.

These data support the etiologic role of bone marrow and erythrocytic parasitization by an unidentified bacterium in systemic lupus erythematosus, and the efficacy of macrolides such as clarithromycin with a rifamycin derivative and/or a third generation cephalosporin with a rifamycin derivative in eliminating these organisms from the erythrocytes and bodies of patients with SLE and related conditions.

The foregoing description and the examples are intended as illustrative and are not to be taken as limiting. Still other variations within the spirit and scope of this invention are possible and will readily present themselves to those skilled in the art.

I claim:

1. A process for treating a patient whose erythrocytes contain exogenous bacterial structures stainable with acridine orange or giemsa and are visible in phase contrast microscopy that comprises administering to said patient an antibacterial amount of a rifamycin plus an antibacterial amount of a macrolide or a third generation cephalosporin until said exogenous bacterial structures are absent from the erythrocytes.

2. The process according to claim 1 wherein a third generation cephalosporin is administered and an adjuvant amount of probenecid is administered in conjunction with said administration of said third generation cephalosporin and a rifamycin.

3. The process according to claim 1 wherein a rifamycin and a macrolide are administered.

4. The process according to claim 1 wherein said administration is repeated periodically.

5. The process according to claim 1 wherein said rifamycin is rifampin or rifabutin.

* * * * *